United States Patent [19]

Jann et al.

[11] Patent Number: 5,189,481
[45] Date of Patent: Feb. 23, 1993

[54] PARTICLE DETECTOR FOR ROUGH SURFACES

[75] Inventors: Peter C. Jann, Santa Clara; Kenneth P. Gross, San Carlos; Armand P. Neukermans, Palo Alto, all of Calif.

[73] Assignee: Tencor Instruments, Mountain View, Calif.

[21] Appl. No.: 736,517

[22] Filed: Jul. 26, 1991

[51] Int. Cl.$^5$ .............................................. G01N 21/88
[52] U.S. Cl. ...................................... 356/73; 250/572; 356/237
[58] Field of Search .................. 356/237, 445, 73; 250/563, 571, 572

[56] References Cited

U.S. PATENT DOCUMENTS

| | | | |
|---|---|---|---|
| 3,857,637 | 12/1974 | Obenreder | 356/237 X |
| 4,069,484 | 1/1978 | Firester et al. | 356/237 X |
| 4,614,427 | 9/1986 | Koizumi et al. | 356/73 X |
| 4,740,708 | 4/1988 | Batchelder | 356/237 X |
| 4,902,131 | 2/1990 | Yamazaki et al. | 356/237 X |

FOREIGN PATENT DOCUMENTS 63-67549  3/1988  Japan .................................. 356/237

OTHER PUBLICATIONS

R. Browning et al., "Recent advances in automated patterned wafer inspection," *SPIE Proceedings*, vol. 1087, pp. 440-445 (1989).

Tencor Instruments, *Surfscan 7000 Patterned Wafer Contamination Analyzer*, (product brochure), Mar. 19909.

*Primary Examiner*—Vincent P. McGraw
*Attorney, Agent, or Firm*—Schneck & McHugh

[57] ABSTRACT

A surface inspection apparatus having multiple inspection stations to inspect a wafer for a number of characteristics. The wafer is placed on a chuck connected to a rack-and-pinion or equivalent system so that the wafer simultaneously rotates and translates under the fixed position of the inspection stations. A single light source may be used by all stations in turn. One station may be a particle detector with collection optics receiving a small select portion of the light scattered from the wafer surface. A second station may be a roughness detector with a collection system to direct a large portion of scattered light to a detector. A position sensitive detector may be used to determine the slope of the wafer surface at an inspection point when the wafer is not clamped to the chuck, giving a measure of surface deformation. These or other stations are positioned about either of two inspection points at which the beam from the light source may be directed. The inspection points are spaced one wafer radius apart to minimize the required wafer motion for a complete surface scan.

14 Claims, 4 Drawing Sheets

PARTICLE DETECTOR FOR ROUGH SURFACES

TECHNICAL FIELD

The present invention relates to optical measuring and testing apparatus for inspecting surfaces for the presence of particles, surface defects and the like, and in particular to such apparatus that employ scattering of a light beam by the particles or defects in order to detect them.

BACKGROUND OF THE INVENTION

Over the last few years, the need has arisen in the semiconductor industry for inspection of unpatterned wafers which have a relatively rough surface as compared to regular monitor wafers, which are highly polished, specularly reflective wafers. Whereas the latter are typically bare unprocessed wafers, the former have usually been subjected to one or several process steps, frequently deposition of either dielectric or metallic layers.

In principle such substrates may be inspected with the present bare wafer inspection instruments. However, it is generally found that the results are disappointing. For maximum sensitivity, these instruments are optimized to collect nearly all scattered light from the inspected surface. The surface roughness on these rough wafers gives rise to a large and often strongly fluctuating background, which tends to obscure the response of small particles.

In recent years, patterned wafer inspectors, such as the Tencor 7000, have been developed for inspecting very rough surfaces. Here the roughness is a result of the structured topography of the patterns themselves, rather than from microscopic surface or film roughness. The nature of the scatter on these surfaces dictates a set of conditions which is sometimes extreme, and therefore drastic measures must be taken in order to discriminate against or eliminate the background scatter. In this process the light from small particles may get reduced to a level which makes detection difficult if not impossible. In practice it is indeed found that these instruments cannot detect particles as small as can be detected by a bare wafer scanner (at best they can detect 0.4 to 0.5 micron particles on a relatively smooth surface versus 0.1 micron for bare wafer scanners). In addition, the presence of the periodic patterns requires electronics and algorithms, which significantly increases the complexity and hence the cost of the instrument. There exists therefore a need for an instrument which has better sensitivity and is simpler than patterned wafer detectors for use on unpatterned but rough wafers, and with sensitivity approaching the bare (smooth) wafer scanners, if possible.

Moreover during the last two years, interest has arisen in cluster-tool type processing equipment, which allows a sequence of processing steps and a degree of cleanliness which cannot be accommodated in classical processing equipment. Associated with this cluster type processing equipment is a new kind of cluster type measurement instrumentation.

Very often the requirements for this type of instrumentation are vastly different from the classical case. It is not uncommon that the measurement is required to take place in vacuum, which places severe restriction on the type of equipment which can be used. The measurement equipment is very often dedicated to the particular cluster, which necessitates a large number of instruments in any single fab. Hence, it is desirable to design instruments which are very compact, highly reliable and relatively inexpensive to fabricate and to maintain.

Preferably, the instrument should have multiple measurements capability. For example, in inspecting a deposited dielectric film, it may be desirable to measure not only the number of particles inadvertently deposited in or upon the film, but also its surface roughness, reflectance, film thickness and if applicable film stress. It is therefore very desirable that these instruments use a common platform, and use as many parts and functions in common as possible to perform these tasks.

SUMMARY OF THE INVENTION

The object has been met with a surface inspection apparatus in which multiple inspection stations collect and detect light from spaced apart positions on the wafer while the wafer simultaneously rotates and translates under the fixed positions of the incident light beams. A chuck supports a workpiece having a substantially planar surface, such as a wafer. The surface is to be inspected for a number of characteristics, such as the presence (or absence) of particles at each location on the surface, the surface roughness of the wafer, the amount of deformation of the wafer from a plane, and the like. A rack-and-pinion system, or other means, connected to the chuck is used to simultaneously rotate the chuck about its central axis and translate it along a path relative to a fixed reference position. A light source, such as a laser, provides a light beam, which is directed by an inspection station to a fixed position, such that the beam is incident upon the wafer surface and describes a spiral on the wafer as the chuck moves in its simultaneous rotational and translational manner. A second inspection station would direct the beam to another fixed position spaced apart from the first fixed position, preferably by a distance substantially equal to the radius of the wafer so that the required translation of the chuck for complete scanning by a beam is minimized. Each inspection station has collection optics and a light detector for receiving a portion of the light from the corresponding fixed position on the surface. The detector provides an electrical signal indicative of a characteristic of the surface which is being inspected. For example, if the collection optics is such that the detector receives only light scattered in a cone centered on a cone axis at an angle to a plane of incidence of the light beam, the optics will discriminate light scattered from particles on the surface from light scattered or reflected from other surface features, and the detector will provide a signal indicative of the presence or absence of particles at the point on the surface where the light beam is incident. A collection optics system that collects a substantial portion of the scattered light will cause the detector to provide a signal proportional to the scattering intensity and hence indicative of the overall surface roughness at the point of incidence of the light beam. A position sensitive detector, fixed in a position to detect specularly reflected light from the beam whenever the local surface at the incidence point is in a certain orientation, can be combined with means connected to the chuck for varying the orientation of the wafer surface. The orientation gives a measure of the surface deformation at the incidence point of the light beam. Other inspection stations using specularly reflected light can also be included to measure surface reflectance, film thickness or some other surface characteristic.

BEST MODE FOR CARRYING OUT THE INVENTION

Figure 1:
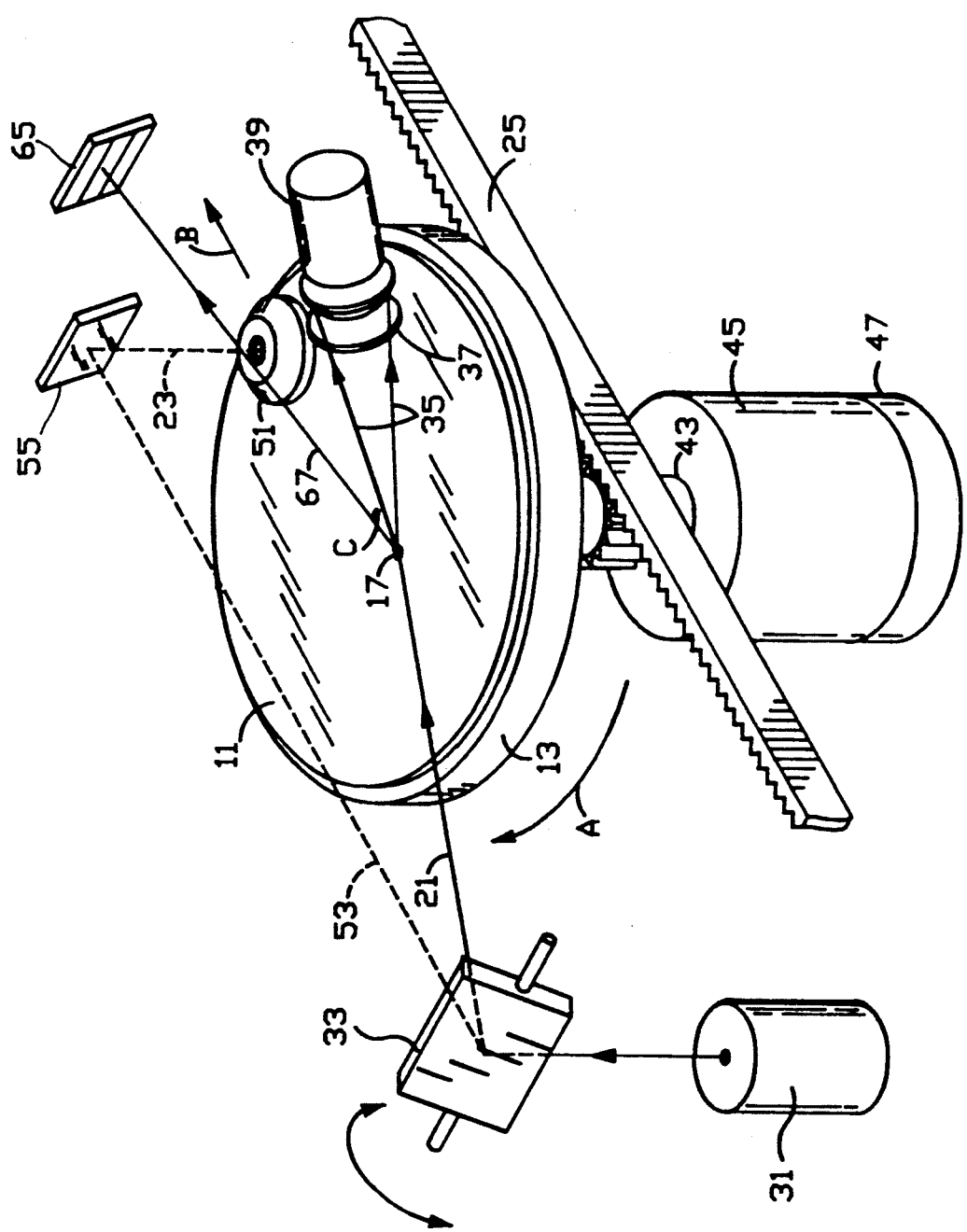
FIG. 1 is a perspective view of a surface inspection apparatus of the present invention.

With reference to FIGS. 1-4, a wafer 11 is positioned on a rotating chuck 13. This chuck either uses a mechanical or electrostatic clampdown in a vacuum atmosphere, or alternatively, when at atmospheric pressure uses a vacuum holddown. The wafer 11 may be coated with dielectrics, such as silicon dioxide or BPSG, polysilicon, or metals such as aluminum or Al-Cu alloys, all giving it a surface with high background scatter. While rotating about a spin axis 15 in a direction A, the wafer 11 is simultaneously translated in a direction B such that any fixed point 17 or 19 in effect describes a tightly wound spiral on the wafer 11. A starting position 11' of the wafer is shown in phantom in FIG. 2. The fixed illumination point 17 starts at the edge of wafer 11', and as the wafer moves under point 17, effectively spirals in toward the center C of the wafer. Likewise, the fixed illumination point 19 starts at the center C of the wafer 11' and effectively spirals out to the edge as the wafer moves. A suitably positioned laser beam 21 or 23 will therefore sequentially illuminate all points on the wafer. Such systems are well known in the art of contamination inspection.

At atmospheric pressure, the advantages of this particular motion system are largely offset by its disadvantages. Mechanical rotation makes for a relatively long measurement time, and further makes it quite difficult to encode the exact position (r, Θ) of a detected particle with enough accuracy so that it can be revisited to identify the particle. In a vacuum however, the simplicity of the mechanical motion, and the small space occupied by the mechanism largely compensate for the above deficiencies. For an instrument dedicated to a cluster tool, throughput is usually not an overwhelming concern, while space is extremely important. It should be readily recognized that, with this kind of simultaneous rotating and translating arrangement, the mechanical displacement of the wafer 11 only needs to equal its radius. By contrast, this displacement would have to equal the wafer diameter in linear scanning systems. Hence there is a substantial reduction in space. By coupling the rotation to the linear displacement with a simple backlash free gear 25, in rack and pinion fashion, both are locked together so that no slippage occurs, as might be the case if two independent drives were chosen. The high inertia of the rotating chuck 13 also provides for a smooth linear translation if this configuration is chosen.

As illustrated, the wafer 11 may be illuminated obliquely with a light beam 21. The beam 21 can be directed by a mirror 33 to a fixed point 17 so that the wafer 11 rotates and translates under it. Preferably, the beam 21 has a relatively short wavelength. For example, an argon ion laser 31 (488, 364 or 351 nm) could be used. The beam diameter may be on the order of 30 μm. Other light sources 31 such as He-Cd, frequency doubled diode lasers and frequency upconverted solid state lasers could also be selected. Preferably, the incoming beam 21 is s-polarized. The direction of the propagation vector should intercept the axis of rotation 15 of the chuck 13 so that the rotation axis 15 is in the plane of incidence. In this way, the intersection 17 of the beam 21 with the plane of the wafer forms an elliptical spot with its major axis oriented in the radial direction B and its minor axis along the direction of wafer motion perpendicular to direction B. For example, if "a" is the beam diameter for an incoming circular beam, then the dimensions of the elongated spot in the plane of the wafer are respectively "a" and "a/sin $\phi$" where "$\phi$" is the angle of incidence. The angle of incidence $\phi$ of the laser beam may vary, depending on the expected condition of the substrate, but typically will be between 5 and 20 degrees with respect to the plane of the wafer 11. For a 30 μm diameter beam incident on the wafer at an angle $\phi$ of 15° above the wafer surface, the dimensions of the elliptical spot will be about 30 by 116 μm.

The radial increment for each turn of the spiral must therefore be a small fraction of this dimension in order to have uniform detection sensitivity over the wafer 11, say one quarter of the above distance of 116 μm, i.e. 29 μm. A motor 41 with a spindle 43 rotates the chuck 13. An encoder 47 is provided with the motor 41 to provide position information Θ about the location of the particle. By providing some reference marks on the wafer 11, and keeping track not only of the number of turns but also of the angular position 8 of the wafer 11 it is possible to reconstruct the position (r, Θ) of individual particles with respect to the reference marks, if so desired.

The scattered light 35 is picked up in a direction orthogonal to the illumination. Typically, only s-polarized light is detected, by using an appropriate polarization filter 37, although combinations of both s-and p-polarized light may be used. Typically, a light collection system 39 is used that has a larger numerical aperture than would be the case for inspecting patterned wafers. This is possible, because, although these wafers have substantial roughness, scattering from them is less pronounced than from patterned wafers. A typical value for the elevation of the center of the receiving system is 25 degrees. Here again, optimum values depend on the expected conditions of the substrate. The numerical aperture of the receiving system 39 would typically be 0.5, corresponding to a half-angle of 30 degrees. Since the wafer 11 is simultaneously rotating and translating, both the illumination system 31 and 33 and the collection system 39 can be axially symmetrical and stationary, making them both very compact. The apparatus performs the particle detection on wafers exhibiting a great deal of surface roughness.

In some cases the measurement of this roughness is also of considerable interest to the device manufacturer. One way to measure roughness is to measure the total integrated scatter (often referred to as TIS), which can then be correlated to the surface roughness in well known ways. The first inspection station 39 catches only a very small fraction of this scatter, as the primary design consideration is in fact elimination of this background.

Figure 2:
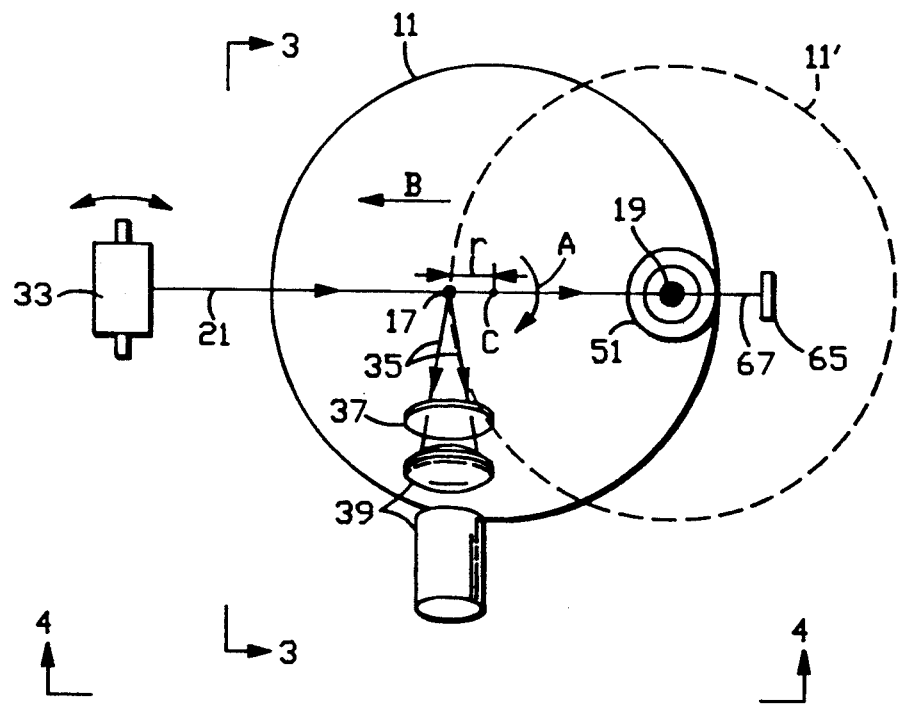
FIG. 2 is a top plan view of the apparatus of FIG. 1.
Figure 5:
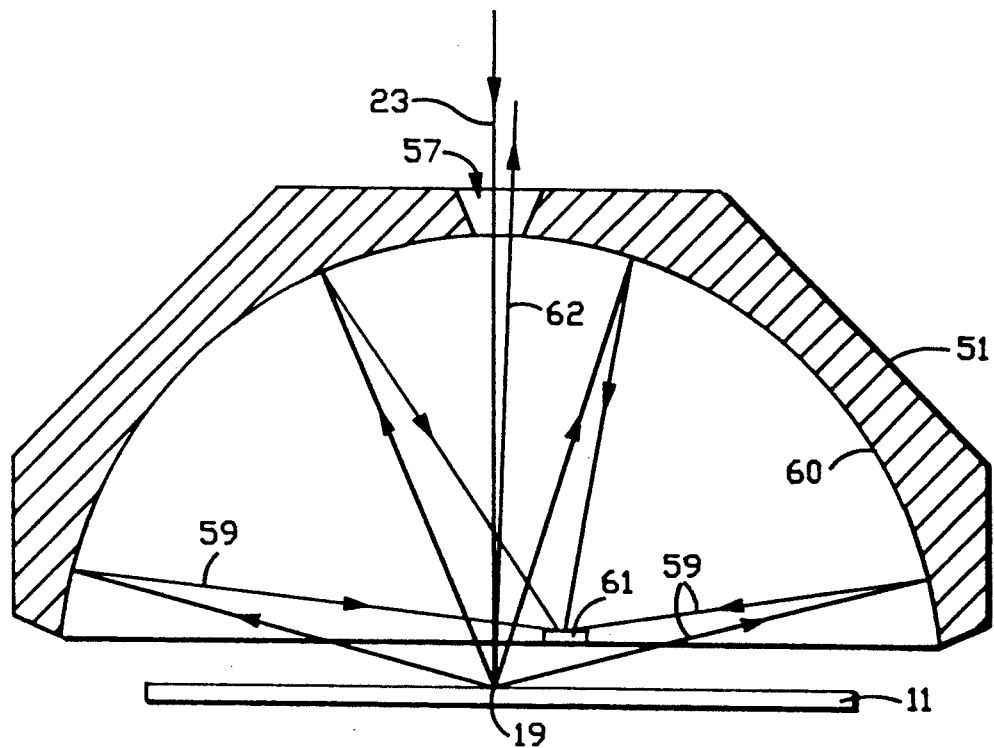
FIG. 5 is an enlarged side section of an inspection station for detecting surface roughness in the apparatus of FIG. 1.
Figure 3:
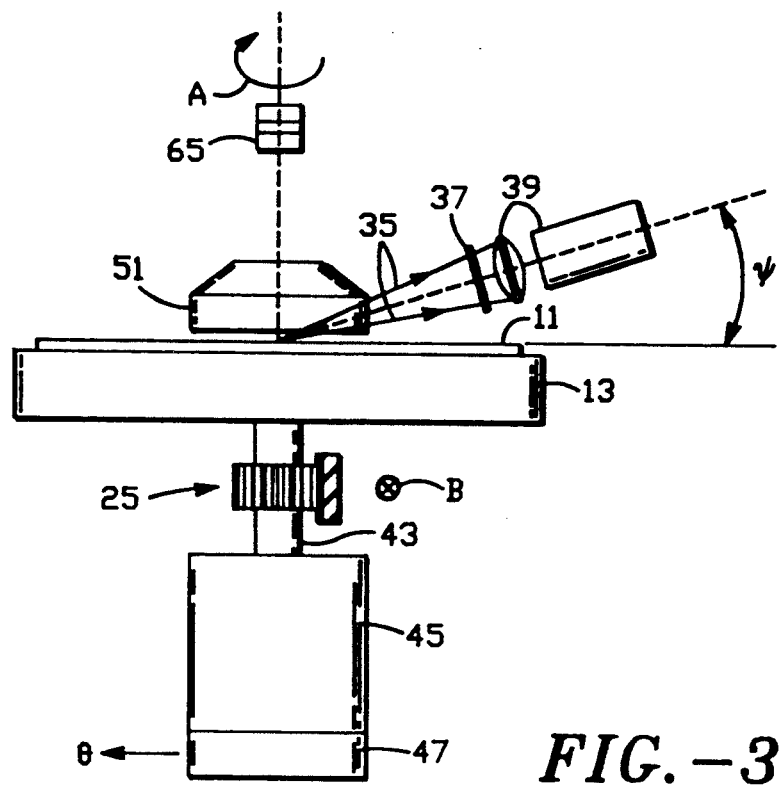
FIGS. 3 and 4 are side views of the apparatus of FIGS. 1 and 2 taken on respective lines 3—3 and 4—4 in FIG. 2.
Figure 4:
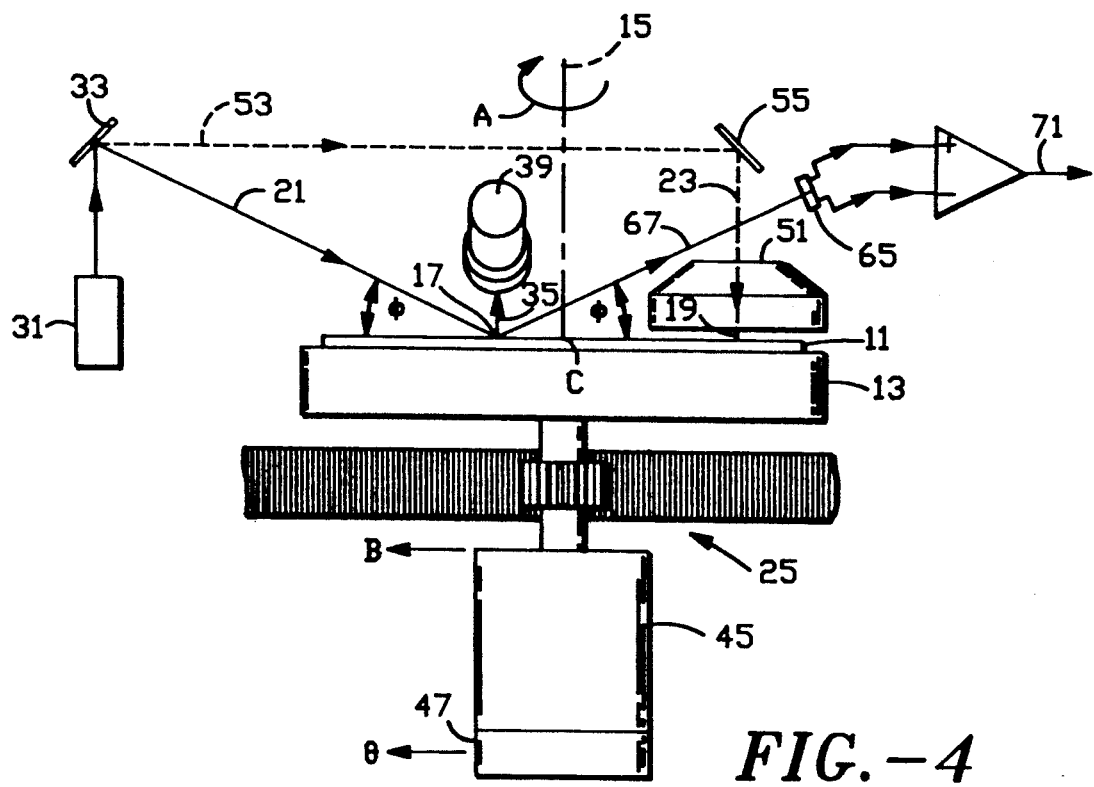

Preferably another collector system 51 is used. FIG. 5 illustrates a case where normal illumination and a Coblentz sphere 51 are utilized for light collection. Alternatively, a single or double parabolic collector may be used. The same laser 31 may or may not be used in this application. The mirror 33 may, for example, pivot in order to direct the beam along an alternate path 53 to a mirror 55. The mirror 55 would then reflect the beam 23 downward at approximately normal incidence through an aperture 57 in the Coblentz sphere 51. To collect data with the same laser 31, the two impact points 17 and 19 of the beams 21 and 23 may be positioned as illustrated in FIG. 2. In this case the rotation angle Θ is the same for both measurement points, and the radial displacement r is equal to the radius of the wafer. This results in easy coordinate transformations and allows for covering the entire surface of the wafer 11 with both detectors with one scan mechanism. The Coblentz sphere configuration 51 corresponds to the one which is used in ASTM F1048-87 (although with a stationary sample) and therefore the results obtained can be directly expressed in terms of this standard. This setup can also be used for particles on smooth bare wafers as will now be described.

The collection efficiency for light of a scattered particle, in the case of the oblique incidence of the first collector system 39 illustrated in FIG. 1, is less than optimal. Its main purpose and advantage is that the scattering of the rough substrate is even more reduced. Therefore these systems are not as sensitive as the configurations used in normal incidence. In the Coblentz sphere arrangement, diffusely scattered light 59 is directed from the inspection point 19 on the wafer 11 to a detector 61, via imaging off of the inner spherical mirror surface 60 of the Coblentz sphere 51. The specularly reflected light beam 62 exits the Coblentz sphere 51 through the same aperture 57 that the incident light beam 23 enters, and may be used for other measurements, such as of surface reflectance. The Coblentz sphere arrangement 51 provides for a very large collection angle of the scattered light 59, but the geometry does not provide for much background rejection. It is therefore also well suited for detection of particles on very smooth surfaces.

With the Coblentz sphere arrangement, a very small detector 61 such as a photo diode must typically be used as the available space is very restricted. For measuring slowly varying signals, such as when measuring TIS, a simple photo diode can be used, and the signal processing used can be fairly straightforward. For detection of particles on smooth surfaces in this mode, it may be desirable to use the same signal processing chain as is used in the oblique incidence mode. Since these systems are not operated simultaneously, this is imminently possible.

Figure 6:
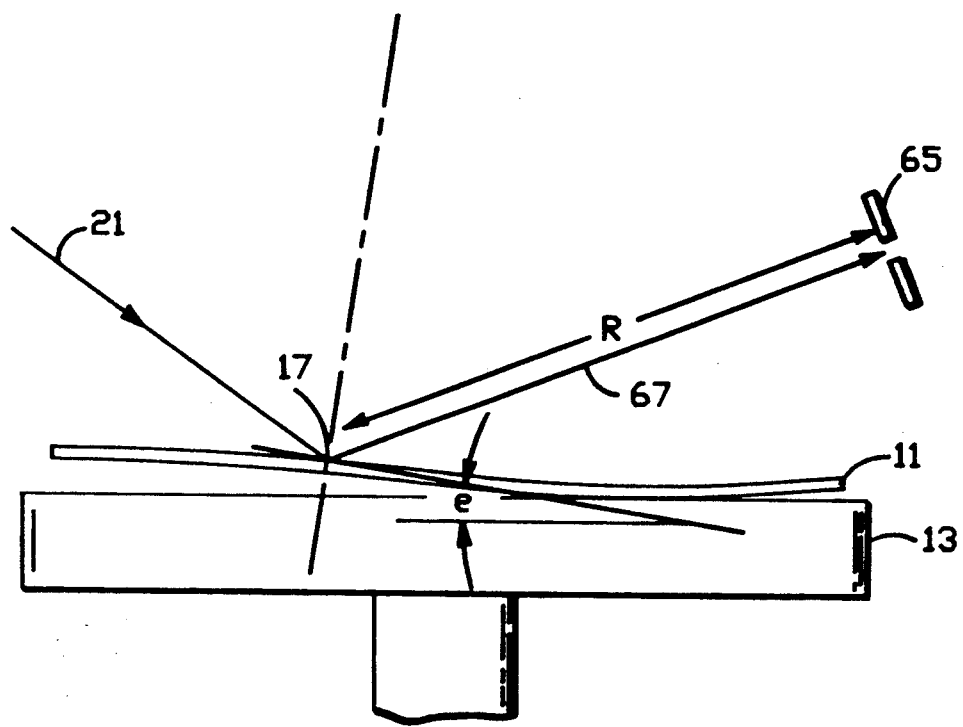
FIG. 6 is a schematic side view of the apparatus of FIG. 1 showing operation of a deformation detector.

With reference to FIG. 6, in order to determine the stress in a deposited layer, it is common to measure the deformation of a wafer 11 caused by the film stress. The wafer substrate is profiled before and after deposition of the film. The incremental bow can be related to the stress present in the film by the following expression:

$$\delta = 3 \left[ (1-\nu)/E9 \right] (t_f/t_s^2) \rho^2 \sigma$$

To perform this measurement, a position sensitive detector 65 is placed in the path of the reflected oblique incident beam 67. The direction of the reflected beam 67 is a function of the local slope of the wafer. A change in the slope e of the substrate 11 will give rise to a change in the beam direction of 2e and a displacement of 2eR on the detector 65, where R is the distance from the point of impingement to the detector 65. Knowing the local slope at each point 17, the surface profile itself can be reconstructed through integration. To make a scan, the wafer 11 may be held in a fixed angular position Θo, and displaced along a radial direction B over a distance equal to the wafer radius, while the beam deflection signal 71 from the detector 65 is recorded. Because with this technique only one side of the wafer 11 is scanned, it is necessary to make several scans, preferably in diametrically opposite directions. By combining the various radial scans, a three dimensional profile can be reconstructed. Because a mechanism displacing the wafer 11 in this manner will not be perfectly straight, it is necessary to first record a baseline with a flat wafer. Alternatively, the same combination of rotation and translation provided by motor 45 and rack-and-pinion drive 25 can be used for the scan, if the rotational speed is not overly fast to cause slippage of the wafer 11 on the chuck 13. Clearly, the wafer 11 cannot be clamped to the chuck in order to perform these measurements, but must be sitting unrestrained in order to get the true stress value.

To measure film thickness, any of a variety of measurement methods could be used, using existing apparatus. By locating the measurement point at the same location as above, the entire area of the wafer can be covered through rotation and translation. The main observation here is that the mechanics necessary for the rough film measurement can be advantageously combined with other measurement types, so that it is easy to obtain multiple capabilities in the same in-line instrument.

The above has illustrated how a simple in-line instrument can be constructed to inspect rough wafers. The wafer is rotated while the measurement point is kept fixed in space. The mechanical elements present on this instrument can be advantageously combined in a variety of instrumental embodiments to measure particles on bare wafers or rough substrates, film thickness or stress as desired.

We claim:

1. A wafer inspection apparatus comprising
    a wafer chuck for supporting a wafer thereon, said wafer having a substantially planar surface to be inspected,
    means connected to said wafer chuck for simultaneously rotating said chuck about a central axis of said chuck and translating said chuck along a path relative to a fixed reference position, said wafer chuck and said motion means disposed in a vacuum environment,
    a light source providing a light beam,
    a first surface inspection station having first means for directing said light beam to a first fixed position, such that said beam is incident upon said surface of said wafer and describes a spiral on said surface as said wafer on said chuck moves, said first surface inspection station also having first means for collecting and detecting a portion of light from said first fixed position, said first means providing a signal indicative of a first characteristic of said surface of said wafer at said first position, and
    a second surface inspection station having second means for direction said light beam to a second fixed position, such that said beam is incident upon said surface of said wafer and describes a spiral on said surface as said wafer on said chuck moves, said second position being spaced apart from said first position, said second surface inspection station also having second means for collecting and detecting a portion of light from said second fixed position, said second means providing a signal indicative of a second characteristic of said surface of said wafer at said second position.

2. The apparatus of claim 1 wherein said first and second fixed positions are located on said path of said chuck.

3. The apparatus of claim 1 wherein said first and second fixed positions are spaced apart by a distance substantially equal to the radius of said wafer.

4. The apparatus of claim 1 wherein one said characteristic of said surface indicated by said signals is a presence of particles at one or more positions on said wafer.

5. The apparatus of claim 1 wherein one said characteristic of said surface indicated by said signals is a surface roughness of said wafer.

6. The apparatus of claim 1 wherein one said characteristic of said surface indicated by said signals is a surface reflectance of said wafer.

7. The apparatus of claim 1 wherein one said characteristic of said surface indicated by said signals is a deformation of said wafer from a plane.

8. The apparatus of claim 1 wherein said light beam is incident upon said surface of said wafer in an incidence plane through said central axis of said chuck.

9. The apparatus of claim 1 wherein said first collecting and detecting means receives only light scattered within a cone centered on a cone axis at an angle to a plane incidence of said light beam, said signal provided by said first collecting and detecting means being indicative of the presence of particles on said surface at said first fixed position.

10. The apparatus of claim 1 wherein said second collecting and detecting means receives a substantial portion of light scattered from said second fixed position, said signal provided by said second collecting and detecting means being a measure of total integrated scatter by said surface indicative of a surface roughness of said wafer at said second fixed position.

11. The apparatus of claim 1 further comprising third means for detecting light specularly reflected from one of said first and second fixed positions of said surface and for providing a signal indicative of a third characteristic of said surface.

12. The apparatus of claim 11 wherein said third characteristic is a surface reflectance of said wafer.

13. The apparatus of claim 1 further comprising means fixed in a position for detecting specularly reflected light from said surface when said surface at a position where said light beam is incident is in a specified orientation, and means connected to said wafer chuck for orienting said wafer on said chuck at said specified orientation for each position of said chuck, said orienting means providing a signal indicative of a deformation of said surface at said beam incidence position.

14. A surface inspection apparatus comprising means for supporting a workpiece having a surface to be inspected for the presence of particles thereon, surface roughness, and the like, said supporting means including means for simultaneously rotating and translating said workpiece in a vacuum environment, a light source providing a light beam, means for directing said light beam along a first light path to said workpiece on said supporting means, said light beam incident on said surface at a fixed first position such that said rotating and translating means causes said light beam to describe a spiral across said surface as said workpiece moves, first means for collecting and deflecting light scattered from said surface at said fixed first position for each position of said workpiece relative to said light beam, said first collecting and detecting means positioned to exclude specularly reflected light and to receive scattered light within a cone centered on an axis at an angle to a plane of incidence of said light beam, said first collecting and detecting means providing a first electrical signal indicative of the presence of particles on said surface, means for directing said light beam along a second light path to said workpiece on said supporting means, said light beam incident on said surface at a fixed second position such that said rotating and translating means causes said light beam to describe a spiral across said surface as said workpiece moves, said second position being separated from said first position by substantially one radius of said workpiece, and second means for collecting and detecting light scattered from said surface at said fixed second position while rejecting specularly reflected light for each position of said workpiece, relative to said light beam, said second collecting and detecting means positioned to receive a substantial portion of said scattered light, said second collecting and detecting means providing a second electrical signal indicative of the surface roughness of said workpiece.

* * * * *

UNITED STATES PATENT AND TRADEMARK OFFICE
CERTIFICATE OF CORRECTION

PATENT NO. : 5,189,481
DATED : February 23, 1993
INVENTOR(S) : Peter C. Jann et al.

It is certified that error appears in the above-indentified patent and that said Letters Patent is hereby corrected as shown below:

Title page, item [56], References Cited, second column, "Tencor Instruments, *Surfscan 7000 Patterned Wafer Contamination Analyzer*, (product brochure), Mar. 19909." should read
- -Tencor Instruments, *Surfscan 7000 Patterned Wafer Contamination Analyzer*, (product brochure), Mar. 1990.- -.

Column 5, line 62, the equation "$\delta = 3 [(1-\nu)/E9 (t_t/t_s^2) \rho^2 \sigma$" should read - -$\delta = 3 [(1-\nu)/E] (t_t/t_s^2) \rho^2 \sigma$- -.

Claim 1, column 6, line 67, "means for direction" should read - -means for directing- -.

Claim 9, column 7, line 34, "plane incidence of said light beam" should read - -plane of incidence of said light beam- -.

Signed and Sealed this

Fourteenth Day of December, 1993

*Attest:*

BRUCE LEHMAN

*Attesting Officer*     *Commissioner of Patents and Trademarks*